(12) United States Patent
Wang et al.

(10) Patent No.: US 12,121,662 B2
(45) Date of Patent: Oct. 22, 2024

(54) SYSTEMS AND METHODS FOR MONITORING THE RESPIRATORY STATUS OF A USER

(71) Applicant: Roam Technologies Pty Ltd., Carlton (AU)

(72) Inventors: Shan-Shan Wang, Sydney (AU); Eugene Weng Hong Lai, Sydney (AU); Gavin Dean May, Sydney (AU); Jay Reginald Flack, Sydney (AU); Jeremy Travis Kwarcinski, Sydney (AU); Sisi Zheng, Sydney (AU)

(73) Assignee: Roam Technologies Pty Ltd., Carlton (AU)

( * ) Notice: Subject to any disclaimer, the term of this patent is extended or adjusted under 35 U.S.C. 154(b) by 0 days.

(21) Appl. No.: 18/385,990

(22) Filed: Nov. 1, 2023

(65) Prior Publication Data
US 2024/0165359 A1    May 23, 2024

Related U.S. Application Data

(60) Provisional application No. 63/384,133, filed on Nov. 17, 2022.

(51) Int. Cl.
*A61M 16/06* (2006.01)
*A61B 5/00* (2006.01)
(Continued)

(52) U.S. Cl.
CPC ..... *A61M 16/0672* (2014.02); *A61B 5/02427* (2013.01); *A61B 5/0816* (2013.01);
(Continued)

(58) Field of Classification Search
CPC ... A61B 5/6819; A61B 5/0261; A61B 5/0295; A61B 5/02; A61M 2230/205;
(Continued)

(56) References Cited

U.S. PATENT DOCUMENTS 5,490,523 A * 2/1996 Isaacson ............ A61B 5/6826
600/323
2004/0230108 A1  11/2004 Melker et al.
(Continued)

FOREIGN PATENT DOCUMENTS

EP    3841974 A1    6/2021

OTHER PUBLICATIONS

Written Opinion of the International Searching Authority for International Application No. PCT/IB2023/060999 dated Feb. 6, 2024 (6 pages).

*Primary Examiner* — Margaret M Luarca
(74) *Attorney, Agent, or Firm* — Finnegan, Henderson, Farabow, Garrett & Dunner, LLP

(57) ABSTRACT

A device for monitoring the respiratory status of a user is disclosed. The device may comprise a nasal cannula comprising a nasal chamber including first and second prongs, a connector configured to couple the nasal cannula to a remote device, and a tube configured to couple the nasal chamber to the connector. The nasal cannula may also comprise optical fibers passing through at least a portion of the tube. A first optical fiber may be configured to transmit light to a first nasal passage of the user, a second optical fiber may be configured to receive light passing through a nose septum and into a second nasal passage of the user.

20 Claims, 13 Drawing Sheets

(51) Int. Cl.
*A61B 5/024* (2006.01)
*A61B 5/08* (2006.01)
(52) U.S. Cl.
CPC ............ *A61B 5/746* (2013.01); *A61B 5/6819* (2013.01); *A61B 2562/0238* (2013.01); *A61M 2202/0007* (2013.01); *A61M 2202/0208* (2013.01); *A61M 2205/0227* (2013.01); *A61M 2205/3306* (2013.01); *A61M 2205/3334* (2013.01); *A61M 2205/50* (2013.01); *A61M 2205/584* (2013.01); *A61M 2210/0618* (2013.01); *A61M 2230/005* (2013.01); *A61M 2230/04* (2013.01); *A61M 2230/20* (2013.01); *A61M 2230/42* (2013.01)

(58) Field of Classification Search
CPC .......... A61M 16/0666; A61M 16/0003; A61M 16/0672; A61M 16/101
See application file for complete search history.

(56) References Cited

U.S. PATENT DOCUMENTS

| | | | | |
|---|---|---|---|---|
| 2009/0107500 A1* | 4/2009 | Edwards | ............ | B01D 53/0446 |
| | | | | 128/205.12 |
| 2014/0180026 A1* | 6/2014 | Melker | ............. | A61M 16/0672 |
| | | | | 600/301 |
| 2017/0319802 A1* | 11/2017 | Holder | .............. | A61M 16/0875 |

* cited by examiner

SYSTEMS AND METHODS FOR MONITORING THE RESPIRATORY STATUS OF A USER

CROSS-REFERENCE TO RELATED APPLICATIONS

The present application claims priority to U.S. Provisional Patent Application No. 63/384,133, filed Nov. 17, 2022, which is incorporated herein by reference in its entirety.

TECHNICAL FIELD

The present disclosure generally relates to systems and methods for monitoring the respiratory status of a user. In particular, embodiments of the present disclosure relate to a device, such as a nasal cannula and/or mask, for monitoring the respiratory status of a user. In addition, embodiments of the present disclosure relate to a system for monitoring the respiratory status of a user and titrating the amount of oxygen delivered to the user to maintain a target oxygen saturation.

BACKGROUND

Conventional pulse oximeters measure a user's heart rate and peripheral oxygen saturation ($SpO_2$) when touch contact is established between the pulse oximeter and the user's skin, such as the user's finger. Conventional pulse oximeters comprise a light source that passes two wavelengths of light through the user's finger and a photodetector that detects the light that passes through the user's skin. Based on the light detected by the photodetector, conventional pulse oximeters can measure the changing absorbance at each of the wavelengths, thereby allowing it to determine the absorbances due to the pulsing arterial blood.

However, conventional pulse oximeters can fall short in accuracy, compliance, and comfort to a patient. For example, fingertip pulse oximeters can easily fall off the user's finger or become misplaced. In addition, when the user's fingers are cold in temperature or have darker skin pigmentation and increased melanin where transmission of light is affected, potentially leading to inaccurate measurements. In order to resolve these issues, pulse oximeters can be clipped onto the user's face, toes, earlobes, forehead and/or the nasal bridge and/or alar. However, because pulse oximeters clipped onto the user's earlobes and/or the nasal alar can be uncomfortable, patient compliance may adversely affect alignment or proper fixation.

Therefore, there is a need for an improved system and method for monitoring the user's respiratory status using pulse oximetry to obtain accurate measurements and simultaneously increase patient compliance. In particular, when the pulse oximeter is coupled with a device for delivering oxygen to the user, an improved system and method for monitoring the user's respiratory status in real-time is necessary in order to provide the correct amount of oxygen back to the user.

SUMMARY

According to the exemplary embodiments of the present disclosure, a device for monitoring the respiratory status of a user is provided. The device may comprise a nasal cannula that is inserted into the nasal passages/nostrils of the user. a connector configured to couple the nasal cannula to a remote device, and a tube configured to couple the nasal chamber to the connector. The device may also comprise a plurality of optical fibers passing through at least a portion of the tube. A first optical fiber of the plurality of optical fibers may be configured to transmit light to the first nasal passage of the user. A second optical fiber of the plurality of optical fibers may be configured to receive light passing through a nose septum and into the second nasal passage of the user.

In some embodiments, the device may further comprise a third optical fiber attached to the tube and configured to emit one or more visible wavelengths of light such that the emitted light is visible from outside the tube. In some embodiments, the third optical fiber may be a side-emitting optical fiber configured to emit different visible wavelengths of light. In some embodiments, a color of the light emitted via the third optical fiber may be indicative of a respiratory status of the user. In other embodiments, the third optical fiber may be configured to emit a first visible wavelength of light when a measured respiratory parameter of the user is within a first range and a second visible wavelength of light when the measured respiratory parameter of the user is within a second range. The first range and the second range may be adjustable by the user or by another user, such as a healthcare provider. In some embodiments, a color intensity, a color pattern, or a timing of the light emitted via the third optical fiber may change based on the respiratory status of the user. In yet another embodiment, the third optical fiber may be configured to emit a third visible wavelength of light when the nasal cannula is incorrectly positioned on the user.

In some embodiments, the connector may comprise at least one of a keyed, barbed receiver or a mechanical or magnetic connector. In some embodiments, the remote device may comprise a light source coupled to the first optical fiber and configured to emit light through the first optical fiber to the first nasal passage of the user and a photodetector coupled to the second optical fiber and configured to receive light passing through the nose septum and through the second optical fiber. The photodetector may be configured to measure a respiratory parameter of the user based on the light received. In some embodiments, the respiratory parameter of the user may comprise at least one of an oxygen saturation ($SpO_2$) level, a heart rate, a perfusion index, a respiratory rate, or a breathing pattern. In other embodiments, the remote device may further comprise a sensor module comprising at least one of a photoplethysmography sensor, a pressure sensor, a temperature sensor, or a humidity sensor.

According to another embodiment of the present disclosure, a device for monitoring the respiratory status of a user is provided. The device may comprise a nasal cannula to be inserted into a second nasal passage of a user, a tube configured to couple the nasal chamber to a connector, and an electronics module mounted on the nasal chamber. The first prong may comprise a light source configured to emit light to the first nasal passage of the user, the second prong may comprise a photodetector configured to detect light passing through the nasal septum and into the second nasal passage of the user, and the photodetector may be further configured to measure a respiratory parameter of the user based on the detected light. The connector may be configured to couple the device to a power source. The electronics module may comprise one or more light sources configured to emit different visible wavelengths of light based on the respiratory status of the user.

According to yet another embodiment of the present disclosure, a system for monitoring the respiratory status of a user and delivering oxygen to the user is provided. The system may comprise a nasal cannula for insertion into the nasal passage of a user and a tube configured to couple the nasal chamber to a connector. The system may also comprise a first optical fiber and a second optical fiber passing through at least a portion of the tube. The system may also comprise a third optical fiber attached to the tube. In addition, the system may comprise a remote device coupled to the nasal cannula via the connector. The remote device may comprise a light source coupled to the first optical fiber and configured to emit light through the first optical fiber to the first nasal passage of the user and a photodetector coupled to the second optical fiber and configured to receive light passing through the nasal septum and into the second nasal passage of the user and through the second optical fiber. The photodetector may be configured to measure respiratory parameters of the user based on the received light.

In some embodiments, the third optical fiber may be configured to emit a first visible wavelength of light when the measured respiratory parameter of the user is within a first range and a second visible wavelength of light when the measured respiratory parameter of the user is within a second range. In other embodiments, the first range and the second range may be adjustable by the user or by another user, such as a healthcare provider. In some embodiments, the third optical fiber may be configured to emit a third visible wavelength of light when the nasal cannula is incorrectly positioned on the user.

In yet another embodiment, the remote device may further comprise of and/or be coupled to an oxygen concentrator or other sources of oxygen delivery, via the nasal cannula, to the user. The oxygen concentrator may be configured to adjust an amount of oxygen delivered to the user based on one or more measured respiratory parameters of the user. The one or more measured respiratory parameters of the user may be at least one of the respiratory parameter measured by the photodetector in the remote device or a respiratory parameter measured by an external device coupled to the remote device. In some embodiments, the connector may comprise at least one of a keyed, barbed receiver or a mechanical or magnetic connector. In some embodiments, the one or more measured respiratory parameters of the user may comprise at least one of an oxygen saturation ($SpO_2$) level, a heart rate, a perfusion index, a respiratory rate, or a breathing pattern. In other embodiments, the remote device may further comprise a sensor module comprising at least one of a photoplethysmography sensor, a pressure sensor, a temperature sensor, or a humidity sensor.

DETAILED DESCRIPTION

Smart Cannula

Figure 1:
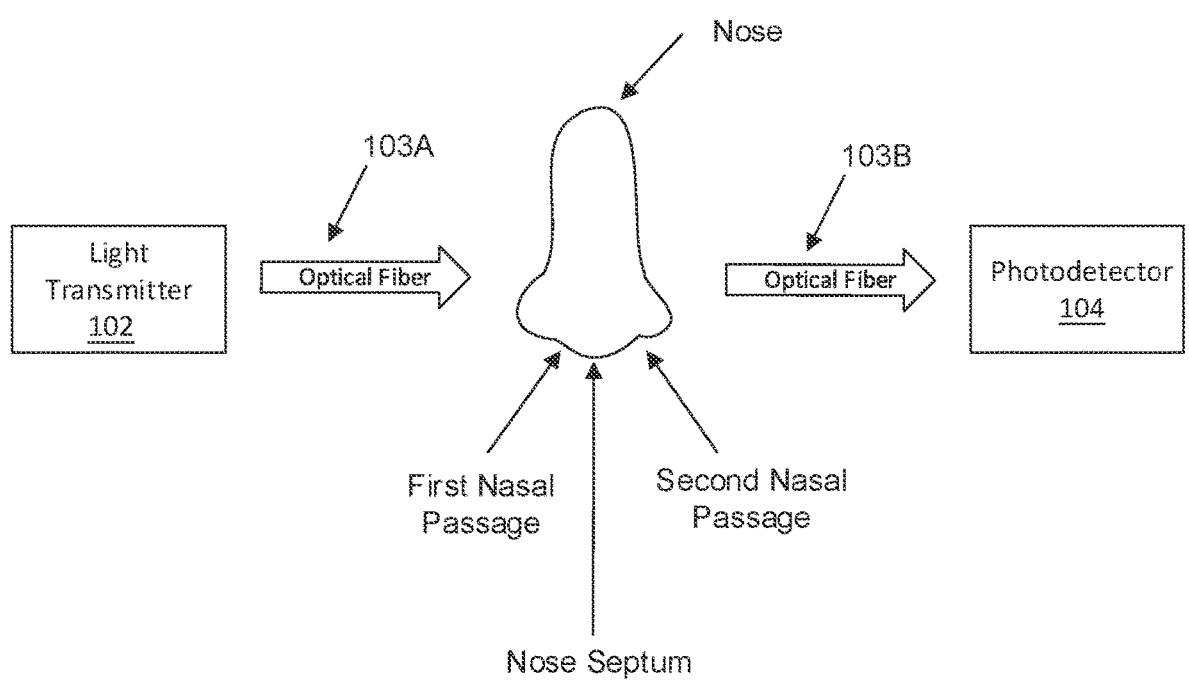
FIG. 1 illustrates a schematic diagram of an exemplary device for monitoring the respiratory status of a user, according to the embodiments of the present disclosure.

The embodiments of the present disclosure provide a system for monitoring the respiratory status of a user with one or more respiratory parameters related to the breathing of the user, such as the user's heart rate, peripheral oxygen saturation (SpO2), and/or respiratory rate. Respiratory status refers to the overall condition and functionality of a person's respiratory system, which includes the lungs, airways, and associated muscles. It encompasses various factors that indicate how well a person is able to breathe and maintain adequate levels of oxygen in the body. These factors can include: Breathing Rate or Respiratory Rate (e.g., the number of breaths a person takes per minute which is an important indicator of respiratory health); Breath Sounds (e.g., abnormal sounds like wheezing, crackles, or stridor can indicate issues with the airways or lung function); Use of Accessory Muscles (e.g., in situations where breathing is difficult, individuals might use extra muscles in the neck or chest to help with the breathing process); Oxygen Saturation or SpO2 (e.g., the percentage of oxygen bound to hemoglobin in the blood); Breath Quality (e.g., the ease and comfort with which a person is able to breathe, for example, shallow, rapid breathing might indicate distress); Cough (the presence of a cough and its characteristics can provide information about respiratory health); etc. Monitoring respiratory status is important in monitoring the health of an individual, especially in cases of illness or injury that affect the respiratory system. It may help healthcare professionals to determine the appropriate interventions and treatments needed to support the individual's breathing and oxygenation.

In some embodiments, the system may comprise a smart nasal cannula configured to measure one or more respiratory parameters to monitor the user's respiratory status and adjust the amount of oxygen delivered to the user based on the user's physiological requirements. The system may be coupled to, for example, a device for providing concentrated oxygen to the user based on demand. As used herein, the term "respiratory status" can include one or more respiratory conditions of a user. In addition, as used herein, the term "respiratory parameter," "one or more respiratory parameters," and "respiratory parameter(s)" may include one or more physiological parameters related to the breathing of a user. For example, a respiratory parameter may be a characteristic associated with the user's respiratory system (e.g., breathing), which includes the lungs, airways, and related organs involved in the process of breathing and gas exchange. These parameters may be indicators of respiratory function and health. Among others, these parameters may include: Respiratory Rate—the number of breaths taken per minute; Tidal Volume (TV)—volume of air inhaled and exhaled during a single breath at rest; Minute Ventilation—total volume of air that is breathed in and out per minute; Vital Capacity—the maximum volume of air a person can inhale and exhale forcefully after taking the deepest breath possible; Forced Expiratory Volume in 1 Second: the amount of air a person can forcefully exhale in one second after a deep inhalation; Peak Expiratory Flow (PEF)—the maximum speed at which a person can exhale air after a maximal inhalation; Functional Residual Capacity (FRC)—the volume of air left in the lungs after a normal, passive exhalation; Total Lung Capacity (TLC)—the maximum amount of air the lungs can hold after a maximal inhalation; Partial Pressure of Oxygen and Carbon Dioxide—the partial pressures of oxygen and carbon dioxide in the blood, respectively; Oxygen Saturation—the percentage of hemoglobin molecules in the blood that are saturated with oxygen, etc.

In some embodiments, the smart nasal canula configured to measure a user's one or more respiratory parameters when touch contact is established with the user's nose along at least a portion of the length of the tube of the nasal cannula. In some embodiments of the present disclosure, the smart cannula may not be limited to a smart nasal cannula and may be a smart cannula configured to measure the user's respiratory parameter(s) when touch contact is established with one or more locations of the user's body. For example, the smart cannula may be configured to be in touch contact with the user's head and/or the user's face and may be configured to measure the user's respiratory parameter(s) when the touch contact is established. In other embodiments, the smart cannula may be integrated with one or more additional sensors (in addition to pulse oximetry) in order to measure other respiratory-related parameters of the user.

In some embodiments, the smart nasal cannula may deliver oxygen while simultaneously measuring the user's respiratory parameters. In some embodiments, the nasal cannula may be illuminated in various colors in order to provide a visual representation of the user's respiratory status and can alert the patient and/or healthcare providers of the user's poor or declining functional status. For example, a side-emitting fiber optic may be attached to the smart nasal cannula to provide this visual indication of the user's respiratory status in real-time. The smart nasal cannula can take pulse oximetry measurements directly across the nasal septum of the user, and in some embodiments, the measurements can be input into an oxygen concentrator or other oxygen source for the purposes of titration. For example, the smart nasal cannula may be coupled to an oxygen concentrator, which may utilize an algorithm to calculate and output the amount of oxygen bolus to cater for user requirement based on the user's monitored respiratory status and/or based on the user's measured respiratory parameter(s).

By way of example, as shown in FIG. 1, a device for monitoring the respiratory status of a user, such as a smart nasal cannula, may comprise a light transmitter 102 configured to transmit, via a first optical fiber 103A, one or more (e.g., a plurality of) wavelengths of light to the user's first nasal passage in the nose. The wavelength(s) of light may pass through the user's nasal septum and into the second nasal passage of the nose. At least a portion of the light that passes into the user's second nasal passage may be received by a second optical fiber 103B and transmitted to a photodetector 104. The device may further comprise at least one processor configured to receive and detect the light and measure the difference in a characteristic of the light (e.g., intensity, wavelength, frequency, color, polarization, phase, direction, speed, polarization state, dispersion, etc.) that was directed into the user's first nasal passage and that was collected from the second nasal passage. For example, the at least one processor may be configured to receive and detect the light and measure the changing absorbance at each of the wavelengths, thereby determining the absorbances due to the pulsing arterial blood alone. In some embodiments, the light transmitter 102, the photodetector 104, and the at least one processor may be housed within the device for monitoring the respiratory status of the user, such as the smart nasal cannula. In other embodiments, the light transmitter 102, the photodetector 104, and the at least one processor may be housed within a remote device coupled to the nasal cannula, such as within an oxygen concentrator coupled to the nasal cannula. In other embodiments, the light transmitter 102 and the photodetector 104 may be housed within the nasal cannula, and the at least one processor may be housed within a remote device coupled to the nasal cannula.

As discussed above, in some embodiments of the present disclosure, the smart cannula may not be limited to a smart nasal cannula and may be a smart cannula configured to measure the user's respiratory parameter(s) related to breathing when touch contact is established with one or more locations of the user's body. For example, the smart cannula may comprise a first prong configured to be disposed on a first location of a body of a user and a second prong configured to be disposed on a second location of the body of the user. By way of example, the first prong may be disposed on a first location of the user's cheek(s) and the second prong may be disposed on a second location of the user's cheek(s). Additionally, or alternatively, the first prong may be disposed on a first location of a rim and/or ridge of the user's nose and the second prong may be disposed on a second location of a rim and/or ridge of the user's nose. Additionally, or alternatively, the front prong may be disposed on a first location of a lobe and/or rim of the user's ear and the second prong may be disposed on a second location of a lobe and/or rim of the user's ear. The smart cannula may comprise a connector (discussed in further detail below) configured to couple the cannula to a remote device. The smart cannula may also comprise a tube configured to couple the first prong and the second prong to the connector. The tube may define a first path between the connector and the first prong and a second path between the connector and the second prong. The smart cannula may also comprise a plurality of optical fibers attached to and/or passing through at least a portion of the tube. As will be discussed in more detail below, the first optical fiber may be configured to transmit, via the first path, light to the first location of the body of the user, the second optical fiber may be configured to receive, via the second path, light received at the second location of the body of the user, and the third optical fiber may be configured to emit one or more visible wavelengths of light along at least a portion of a length of the tube such that the emitted light is visible from outside the tube.

Figure 2:
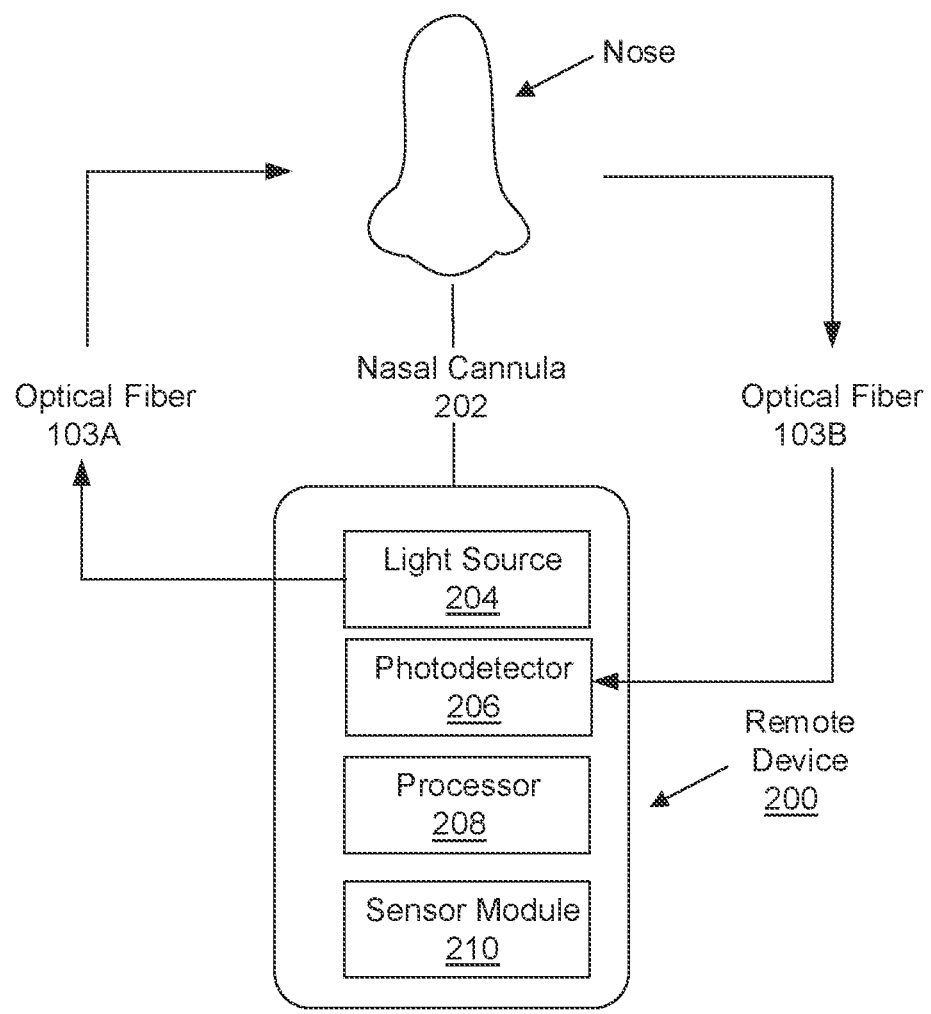
FIG. 2 illustrates a schematic diagram of an exemplary system for monitoring the respiratory status of a user and providing concentrated oxygen, according to the embodiments of the present disclosure.

For example, referring to FIG. 2, an exemplary system for monitoring the respiratory status of a user is provided. As shown in FIG. 2, in some embodiments, a light source 204, a photodetector 206, at least one processor 208, and a sensor module 210 may be housed within a remote device 200, such as an oxygen concentrator (stationary oxygen concentrator or a portable oxygen concentrator), coupled to a nasal cannula 202. The light source 204 may comprise one or more light emitting diodes (LEDs) configured to emit light in the visible spectrum (about 400 nm to about 700 nm) and/or in the invisible spectrum (about 400 nm to about 1 nm, about 2.5 µm to about 750 nm, and/or about 25 µm to about 2.5 µm). The nasal cannula 202 may be attached to the user's nose, such as within a first nasal passage and a second nasal passage of the user's nose. The nasal cannula 202 may comprise the first optical fiber 103A (as shown in FIG. 1 as well) configured to transmit light to the first nasal passage of the user's nose and the second optical fiber 103B (as shown in FIG. 1 as well) configured to receive light passing through the user's nose septum and into the user's second nasal passage. In operation, the light source 204 in the remote device 200 may be configured to beam light of a plurality of wavelengths through the first optical fiber 103A and into the first nasal passage (shown in FIG. 1) of the user's nose. The light may pass through the user's nose septum and into the second nasal passage (shown in FIG. 1) of the user's nose. The second optical fiber 103B may receive the light passing into the user's second nasal passage and transmit that light to the photodetector 206 in the remote device 200. At least one processor 208 may detect the light received by the photodetector 206 and measure the changing absorbance at each wavelength of light. Accordingly, the processor 208 may be configured to measure one or more respiratory parameters of the user based on the received light and determine the user's respiratory status. In some embodiments, the one or more respiratory parameters may comprise, for example, an oxygen saturation ($SpO_2$) level, a heart rate, a respiratory rate, a perfusion index and/or a breathing pattern. As shown in FIG. 2, the remote device 200, such as an oxygen concentrator, may comprise a sensor module 210. The sensor module 210 may comprise, for example, one or more additional sensors, such as a photoplethysmography sensor, a pressure sensor, a temperature sensor, and/or a humidity sensor, or any combination thereof. The sensor module 210 may be configured to measure pressure inside the user's nose to detect risks such as deviated septa, measure air pressure, measure the user's temperature, measure the humidity of the oxygen delivered to the user, or the like.

In some embodiments, the nasal cannula may be attached to the user's nose when operating the oxygen concentrator such that the user's respiratory parameter(s) may be measured continuously and in real-time or near real-time. The oxygen concentrator may be configured to adjust or titrate the oxygen output (e.g., one or more of oxygen concentration, oxygen flow rate, etc.) to the user based on the one or more measured respiratory parameters of the user. For example, the oxygen concentrator may comprise at least one processor that is configured to increase the oxygen output volume when the user's oxygen saturation level is lower than a predetermined range or threshold or decrease the oxygen output volume when the user's oxygen saturation level is higher than a predetermined range or threshold. In other embodiments, at least one processor may be configured to decrease the oxygen output volume to conserve battery power when the user's oxygen saturation level is within a predetermined range.

In some embodiments, the remote device 200 may not be an oxygen source or an oxygen concentrator. By way of example, the at least one processor 208 of the remote device 200 may be configured to monitor the user's respiratory status without providing or adjusting an oxygen output to the user. For example, the remote device 200 may comprise a power source, such as a battery management system (BMS), to provide power to the light source 204, photodetector 206, at least one processor 208, sensor module 210, and nasal cannula 202 without providing any oxygen concentration capabilities. Accordingly, in some embodiments, the remote device 200 and the nasal cannula 202 may both be disposable after use.

Figure 3:
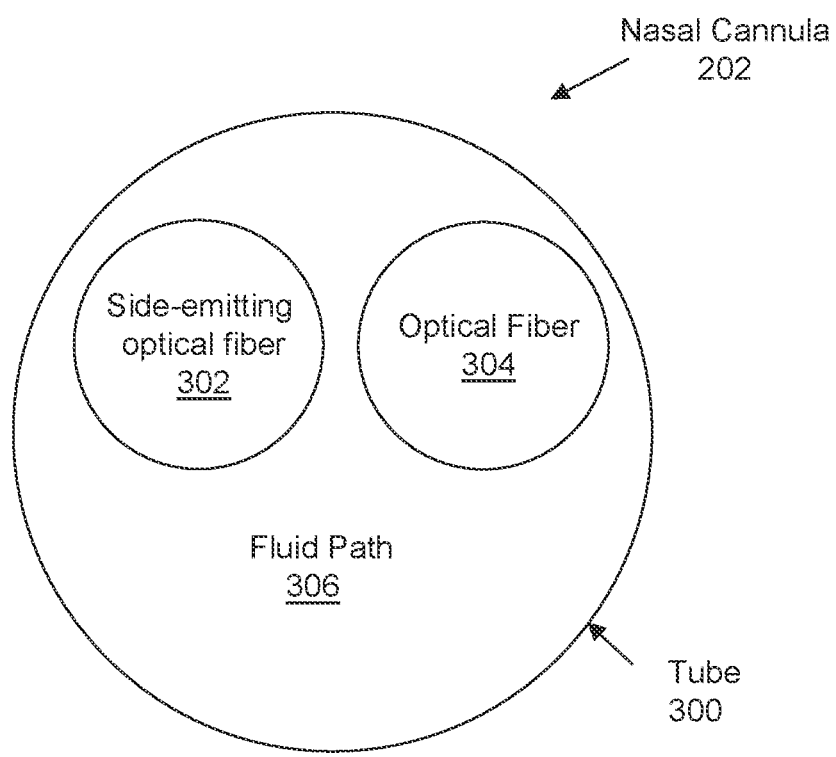
FIG. 3 illustrates a cross-sectional view of an exemplary nasal cannula, according to the embodiments of the present disclosure.
Figure 4:
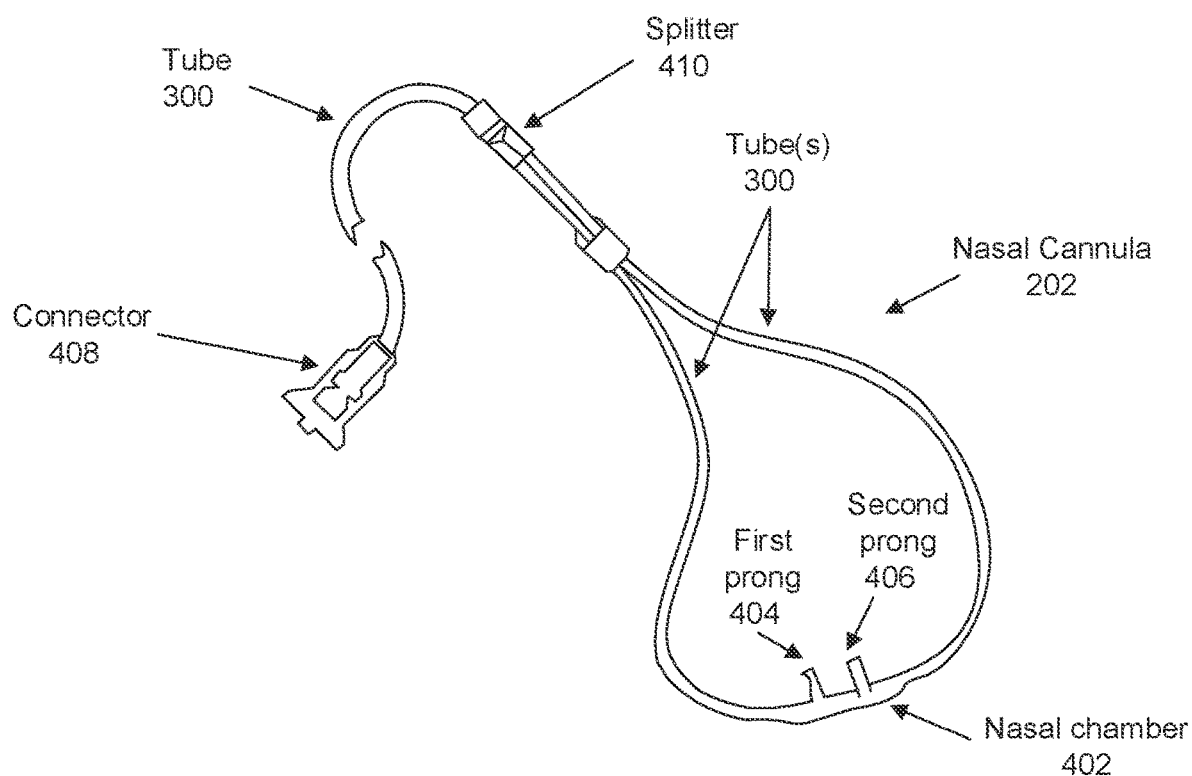
FIG. 4 illustrates an exemplary nasal cannula, according to the embodiments of the present disclosure.

Referring now to FIG. 3, a cross-sectional view of a tube 300 of an exemplary nasal cannula 202 is shown. The nasal cannula 202 may comprise a tube 300 defining a fluid path 306, an optical fiber 304 passing along at least a portion of a length of the tube 300, and a side-emitting optical fiber 302 attached to at least a portion of a length of the tube 300. For example, the side-emitting optical fiber 302 may be attached within the tube 300, attached outside the tube 300, and/or embedded within the walls of the tube 300. The fluid path 306 may be configured to allow gas (such as oxygen) therethrough. For example, when the nasal cannula 202 is attached to the user's nose, the fluid path 306 of the tube 300 may be configured to allow oxygen (or another fluid) to pass therethrough and be provided to the user. The optical fiber 304 may comprise either the first optical fiber 103A of FIGS. 1 and 2 or the second optical fiber 103B of FIGS. 1 and 2. Because the nasal cannula 202 may be attached directly to the user's nose physically, it may reduce the chance of the nasal cannula 202 falling off the user's nose or being incorrectly placed or misplaced, thereby increasing patient compliance, and increasing the accuracy of measurements taken.

In some embodiments, the side-emitting optical fiber 302 may be attached to the tube 300 and may be configured to provide a visual indication of the user's respiratory status. For example, the side-emitting optical fiber 302 may be configured to transmit different visible wavelengths of light along at least a portion of a length of the tube 300 such that the emitted light is visible from outside the tube 300. In some embodiments, the side-emitting optical fiber 302 may be configured to transmit different visible wavelengths of light along the entire length of the tube 300. The different wavelengths/colors of light may provide a visual indication of the user's respiratory status to the user or to another person, such as a clinician, a healthcare provider, caretakers, or the like. By way of example, the side-emitting optical fiber 302 may be configured to transmit green light (or a first light color) along at least a portion of the length of the tube 300 when the user's oxygen saturation level is above a target or optimal $SpO_2$, transmit yellow light (or a second light color) along at least a portion of the length of the tube 300 when the user's oxygen saturation level falls below the target range, and transmit red light (or a third light color) along at least a portion of the length of the tube 300 when the user's oxygen saturation level is below a minimum safety threshold. The various colors of light transmitted by the side-emitting optical fiber 302 are not limited by the embodiments disclosed herein, but the color of light transmitted by the side-emitting optical fiber 302 can be programmed to vary based on the target oxygen saturation level or target range of oxygen saturation level. Moreover, the target oxygen saturation level and/or the target range of oxygen saturation level can be programmed to vary based on each user.

In other embodiments, a color intensity, a color pattern, or a timing of the light emitted via the side-emitting optical fiber 302 may change based on the measured respiratory parameter(s) of the user. In other embodiments, the color intensity, pattern, or timing (e.g., blinking) may be changed to provide a visual indication of emergency low oxygen situations where urgent attention or close monitoring is needed. For example, the side-emitting optical fiber 302 may be configured to transmit red light when the user's oxygen saturation level falls below 80% or has a respiratory rate of greater than 35 bpm or less than 8 bpm or has a heart rate of greater than 130 bpm, or the like. The side-emitting optical fiber 302 may be configured to transmit orange or yellow light when the one or more measured respiratory parameters reflect a moderate or mild level of impairment, or a green light when the one or more measured respiratory parameters are within expected default or programmed normal limits. As discussed above, the various colors of light transmitted by the side-emitting optical fiber 302 are not limited by the embodiments disclosed herein, but the color of light transmitted by the side-emitting optical fiber 302 can be programmed to vary based on the one or more measured respiratory parameters of the user. In some embodiments, these ranges and thresholds are exemplary only, can be changed, and personalized to suit each user's respiratory status. For example, a patient with a known severe lung disease may have an oxygen saturation of 92% under the best circumstances and the oxygen saturation level may routinely drop to about 88% when moving without any distress. Accordingly, the user and/or another user may be able to adjust and personalize the "normal" ranges and thresholds and the at least one processor 208 of the remote device 200 of FIG. 2 may be configured to program the ranges and thresholds for each user accordingly based on the user's needs and preferences.

In yet another embodiment, a color intensity, a color pattern (such as static or flashing/dynamic pattern), or a timing of the light emitted (such as flashing over a time period between seconds and/or minutes) via the side-emitting optical fiber 302 may be changed to indicate a change in respiratory status or situation of the user or based on the surrounding environment (such as day and night environments). By way of example, in a mass casualty situation, the side-emitting optical fiber 302 may be configured to transmit a static red light to indicate a need for immediate assistance, a static yellow light to indicate a need for continuous monitoring or observation, a static green light to indicate a need to wait for further observation, a static white light to indicate that assistance is not required, or a blue light flashing in timed intervals to indicate that the sensors are no longer detecting respiratory parameter(s) which may indicate the cannula has been dislodged or worst case that the user has deceased. In these mass casualty situations, using the side-emitting optical fiber 302 to transmit different types of light may be advantageous because, unlike audible signals such as alarms, different types of light may be more easily differentiated and identified where it is loud or where there is more than one distressed user in an area. In some embodiments, the side-emitting optical fiber 302 may be configured to transmit different types of light to indicate a need for immediate assistance, and an audible signal such as an alarm may be triggered in conjunction with the transmitted light.

In some embodiments, the side-emitting optical fiber 302 may be coupled to one or more light-emitting diodes (LEDs), such as RGB LEDs, housed within the remote device 200 of FIG. 2. The at least one processor 208 may be configured to transmit a light signal from one or more of the LEDs and through the side-emitting optical fiber 302 to provide a visual indication of the user's respiratory status. As discussed above with reference to FIG. 2, at least one processor 208 may also be configured to measure the user's respiratory parameter(s) based on the light received by the photodetector 206 via the second optical fiber 103B. Accordingly, the at least one processor may be configured to receive light from the second optical fiber 103B and transmit light through the side-emitting optical fiber 302 simultaneously so as to provide a real-time or near real-time visual indication of the user's respiratory status.

Figure 9:
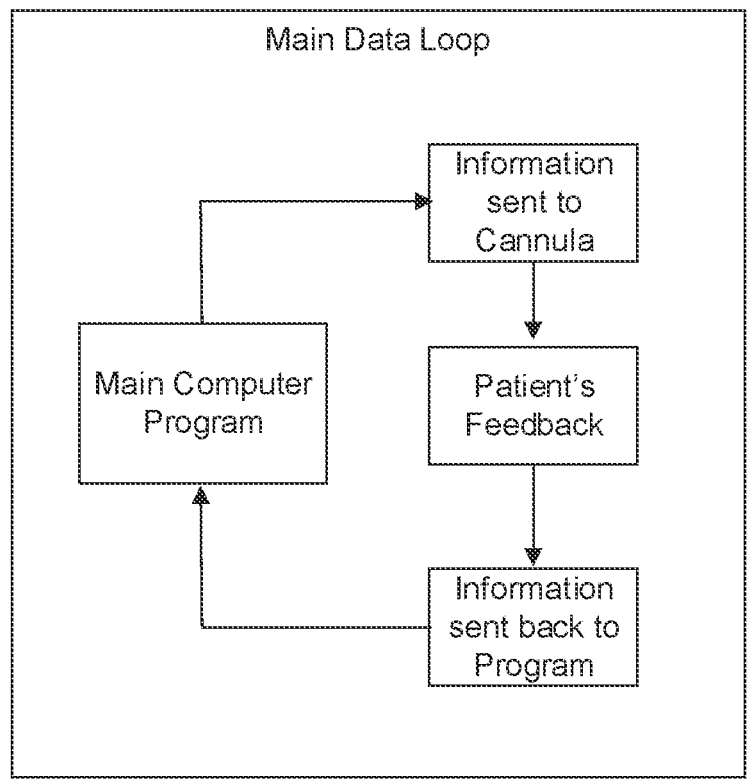
FIG. 9 illustrates a schematic diagram of an exemplary method for monitoring the respiratory status of a user and providing a visual indication of the user's oxygen saturation, according to the embodiments of the present disclosure.
Figure 9:
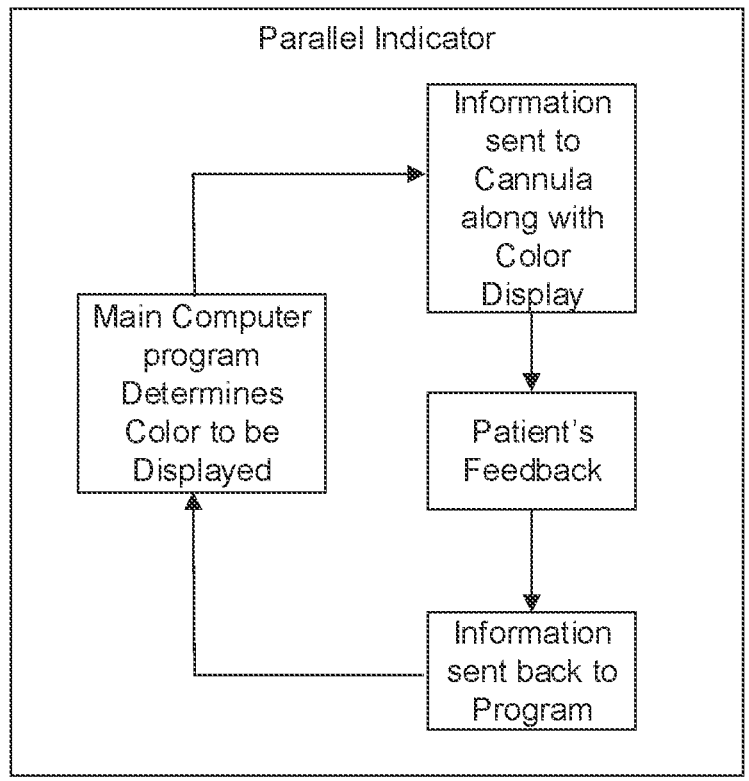

By way of example, FIG. 9 provides a schematic diagram of an exemplary method for monitoring the respiratory status of a user and providing a visual indication of the user's respiratory status, according to the embodiments of the present disclosure. The at least one processor 208 of the remote device 200 may execute a computer program or software design that utilizes a main data loop and a parallel indicator to provide a real-time or near real-time visual indication of the user's respiratory status. As shown in FIG. 9, in the main data loop, the at least one processor 208 may execute the computer program to receive the light signal from the nasal cannula 202 and adjust or titrate the oxygen output to the user based on the respiratory parameter(s) measured using the received light signal. Additionally, or alternatively, at least one processor 208 may be configured to adjust or titrate the oxygen output to the user based on respiratory parameter(s) measured by one or more external devices coupled to the remote device 200. In the parallel indicator, the at least one processor 208 may execute the computer program to receive the light signal from the nasal cannula 202 and determine a color, a color intensity, a color pattern, and/or a timing of the light to be emitted via the side-emitting optical fiber 202 to provide a visual indication of the user's respiratory status in real-time or near real-time. The computer program shown in FIG. 9 may be pre-programmed into an electronic package or a mobile application to be executed on the remote device 200. The computer program may be restricted in operation to the user and/or another person.

Referring now to FIGS. 4-8, an exemplary device for monitoring the respiratory status of a user, according to the embodiments of the present disclosure, is shown. The device may comprise a nasal cannula 202 comprising a nasal chamber 402 including a first nasal prong 404 configured to be placed within a first nasal passage of the user and a second nasal prong 406 configured to be placed within a second nasal passage of the user. The nasal cannula 202 may further comprise one or more tubes 300 connecting the nasal chamber 402 to a connector 408. The connector 408 of the nasal cannula 202 may be configured couple the nasal cannula 202 to a remote device, such as remote device 200 of FIG. 2. In some embodiments, the nasal cannula 202 may also comprise a splitter 410 configured to split the one or more tubes 300, thereby providing a first path for a first optical fiber, such as first optical fiber 103A, to pass along the tube 300 from the connector 408 to the first prong 404 and a second path for a second optical fiber, such as second optical fiber 103B, to pass along the tube 300 from the connector 408 to the second prong 406. Accordingly, the first optical fiber, such as first optical fiber 103A and/or the second optical fiber, such as second optical fiber 103B may be configured to pass along the path, such as fluid path 306, defined by each tube 300. A third optical fiber, such as the side-emitting optical fiber 302, may be attached to each tube 300.

Figure 5:
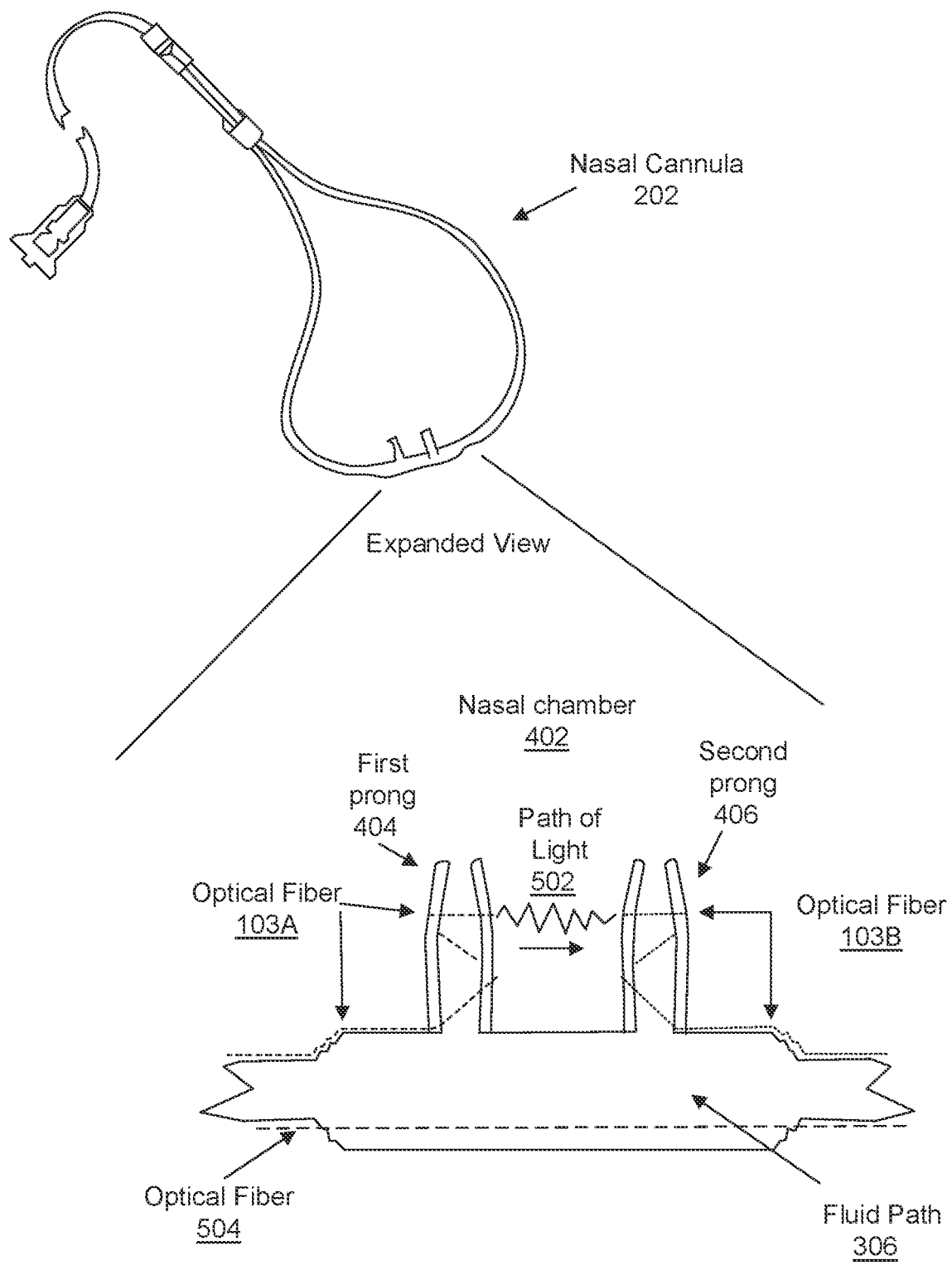
FIG. 5 illustrates an expanded view of an exemplary nasal chamber of the nasal cannula of FIG. 4, according to the embodiments of the present disclosure.

Referring now to FIG. 5, an expanded view of the nasal chamber 402 is shown. As discussed above, the nasal cannula 202 may comprise one or more tubes 300 defining one or more fluid paths 306 to deliver oxygen to the first and second nasal passages of the user's nose. For example, a first fluid path 306 may extend from the connector 408 to the first prong 404 of the nasal chamber 402 and the second fluid path 306 may extend from the connector 408 to the second prong 406 of the nasal chamber 402. The splitter 410 may be configured to split the fluid path defined by tube 300 into two or more fluid paths 306. On each of the fluid paths 306, an optical fiber may be embedded in a radial construction such that the terminating ends of the optical fibers directly face each other. By way of example, the first optical fiber 103A may be embedded in the first fluid path extending from the connector 408 to the first prong 404 in a radial construction, and the second optical fiber 103B may be embedded in the second fluid path extending from the connector 408 to the second prong 406. The terminating ends of the first optical fiber 103A and the second optical fiber 103B in the first and second nasal prongs 404, 406, respectively, may be configured to directly face each other, as shown in FIG. 5. The first nasal prong 404 may be configured to be placed inside the first nasal passage of the user, and the second nasal prong 406 may be configured to be placed inside the second nasal passage of the user. Accordingly, light transmitted through the first optical fiber 103A into the first nasal passage of the user may be configured to pass directly through the nose septum of the user and into the second nasal passage of the user. The second optical fiber 103B may then receive the light passing into the second nasal passage and transmit the received light to a remote device, as discussed above. In some embodiments, a third optical fiber 504, such as the side-emitting optical fiber 302 may be attached to the tube (e.g., attached within the tube, attached outside of the tube, and/or embedded within the wall of the tube) and emit different visible wavelengths of light to provide a visual indication of the user's respiratory status in real-time or near real-time.

Figure 6:
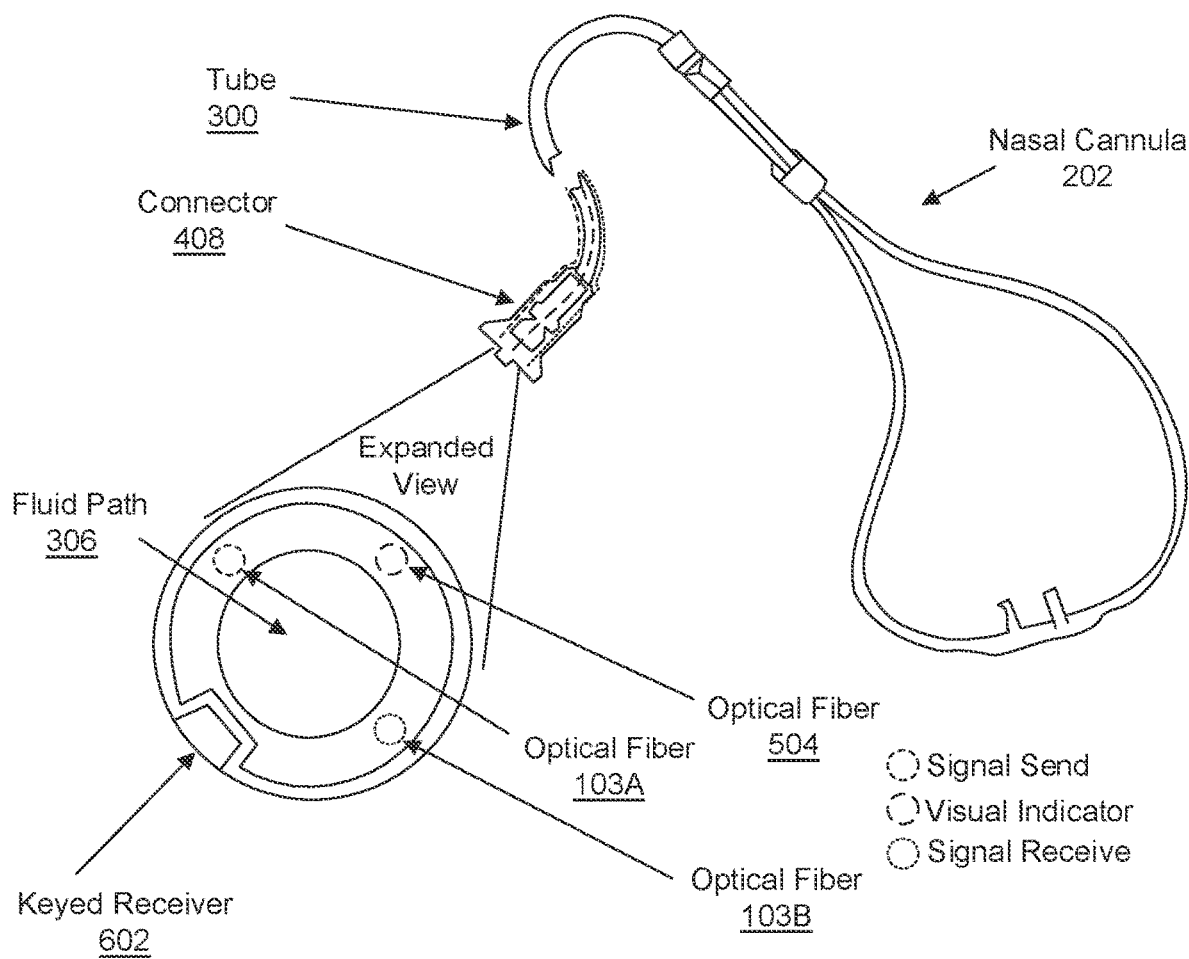
FIG. 6 illustrates an expanded view of an exemplary connector of the nasal cannula of FIG. 4, according to the embodiments of the present disclosure.
Figure 7:
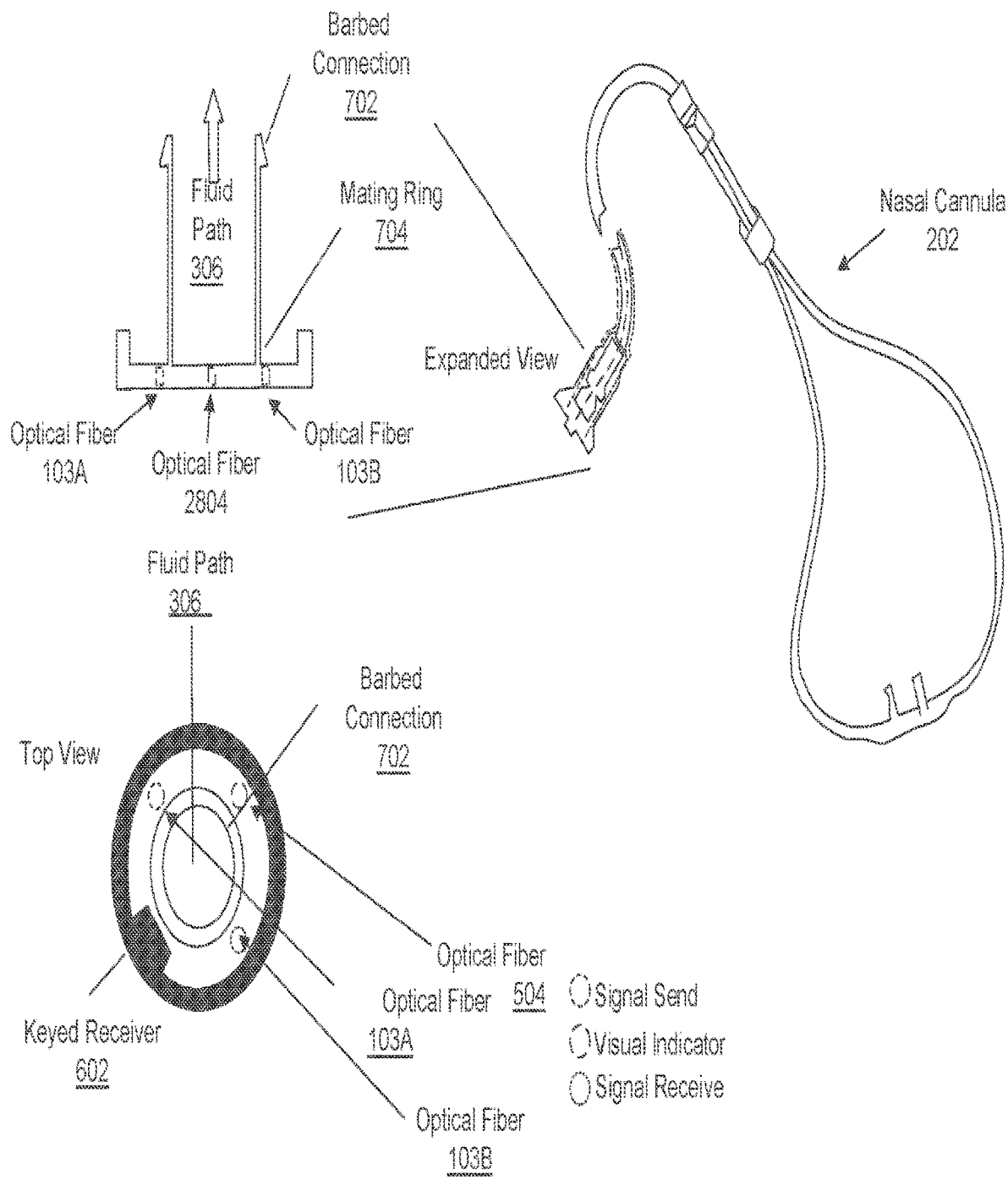
FIG. 7 illustrates an expanded view of another exemplary connector of the nasal cannula of FIG. 4, according to the embodiments of the present disclosure.

In some embodiments, as shown in FIG. 6, the connector 408 of the nasal cannula 202 may comprise a keyed received 602. The keyed received 602 may be configured to obtain a correct orientation and connection between the nasal cannula 202 and a remote device such that the fluid path 306 within the tube 300 is not obstructed. The correct docking arrangement between the nasal cannula 202 and the remote device may also ensure light signals to pass to and from the remote device to the nasal chamber 402 via the first optical fiber 103A, the second optical fiber 103B, and/or the third optical fiber 504 such as the side-emitting optical fiber 302. In other embodiments, as shown in FIG. 7, the keyed receiver 602 may also comprise a barbed connection 702 and a mating ring 704 to form a keyed, barbed receiver. The barbed connection 702 may allow a specific configuration of connection between the nasal cannula 202 and a remote device. Additionally, or alternatively, the first optical fiber 103A, the second optical fiber 103B, and the third optical fiber 504 may be organized in a predetermined configuration within the mating ring 704 to ensure a proper orientation and connection between the nasal cannula 202 and the remote device. Organizing the first optical fiber 103A, the second optical fiber 103B, and the third optical fiber 504 in a predetermined configuration within the mating ring 704 of the connector 408 may allow the device to send and/or receive light signals in specific wavelengths to communicate between the nasal cannula 202 and the processor of the remote device.

In some embodiments, the barbed connection 702 may be a mechanical connection. In other embodiments, the connector 408 may comprise a magnetic connector. The magnetic connector may comprise a magnetic receptacle configured to rely on magnetic force to maintain a connecting contact with the remote device. For example, the remote device may comprise a magnetic plug comprising a magnetic element configured to attach to the magnetic receptacle of the connector 408. The magnetic element may include a permanent rare earth magnet, an electromagnet, or a magnet composed of ferromagnetic material. In other embodiments, the connector 408 may comprise a magnetic plug and the remote device may comprise a magnetic receptacle. When the plug and the receptacle are brought into proximity, the magnetic force and attraction between the magnetic elements in the plug and the receptacle may maintain the connection between the nasal cannula 205 and the remote device.

Figure 8:
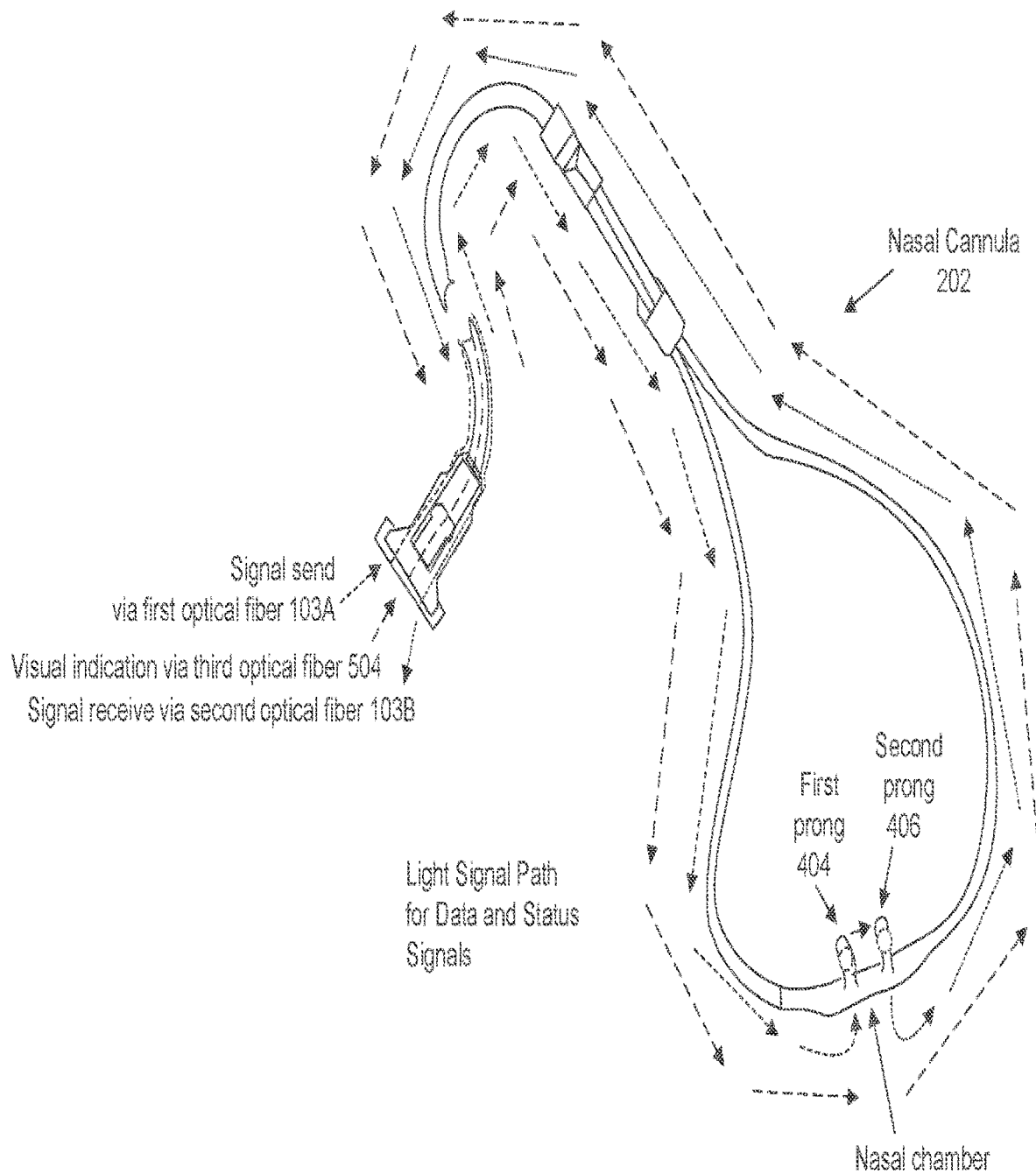
FIG. 8 illustrates exemplary signal pathways of the nasal cannula of FIG. 4, according to the embodiments of the present disclosure.

Referring now to FIG. 8, exemplary light signal paths between a remote device, such as remote device 200, and the nasal cannula 202 is shown. The at least one processor 208 of the remote device 200, for example, may implement a real-time algorithm to send and receive light signals between the remote device 200 and the nasal cannula 202. As discussed above, a light signal of a plurality of wavelengths may be sent via the first optical fiber 103A to the first prong 404 of the nasal chamber 402 and to the first nasal passage of the user. The light may pass through the user's nose septum and into the second nasal passage of the user, in which the second prong 406 is positioned. The light traveling through the nose septum and into the second nasal passage of the user may be transmitted via the second optical fiber 103B back to the photo detector 206 of the remote device 200. Light received by the photodetector 206 and the processor 208 may be analyzed to determine in real-time or near real-time the color, color intensity, color pattern, and/or timing of visible light to be transmitted through or projected through the third optical fiber 504 in order to provide a visual indication of the user's respiratory status.

In some embodiments, the third optical fiber 504 may be used to provide a visual indication of a loss of signal. For example, at least one processor 208 may be configured to detect a loss of signal when the nasal cannula 202 has been dislodged, has been incorrectly positioned on the user's nose, or is otherwise not fitted properly or at all on the user. The processor 208 may emit a visible wavelength of light, such as red or green flashing light, and project the light through the third optical fiber 504 in order to provide a visual indication of the incorrect placement of the nasal cannula 202 and a loss of signal. The processor 208 may also be configured to trigger an external alarm, such as an audible alarm, in the remote device when the processor 208 detects a loss of signal.

Figure 10:
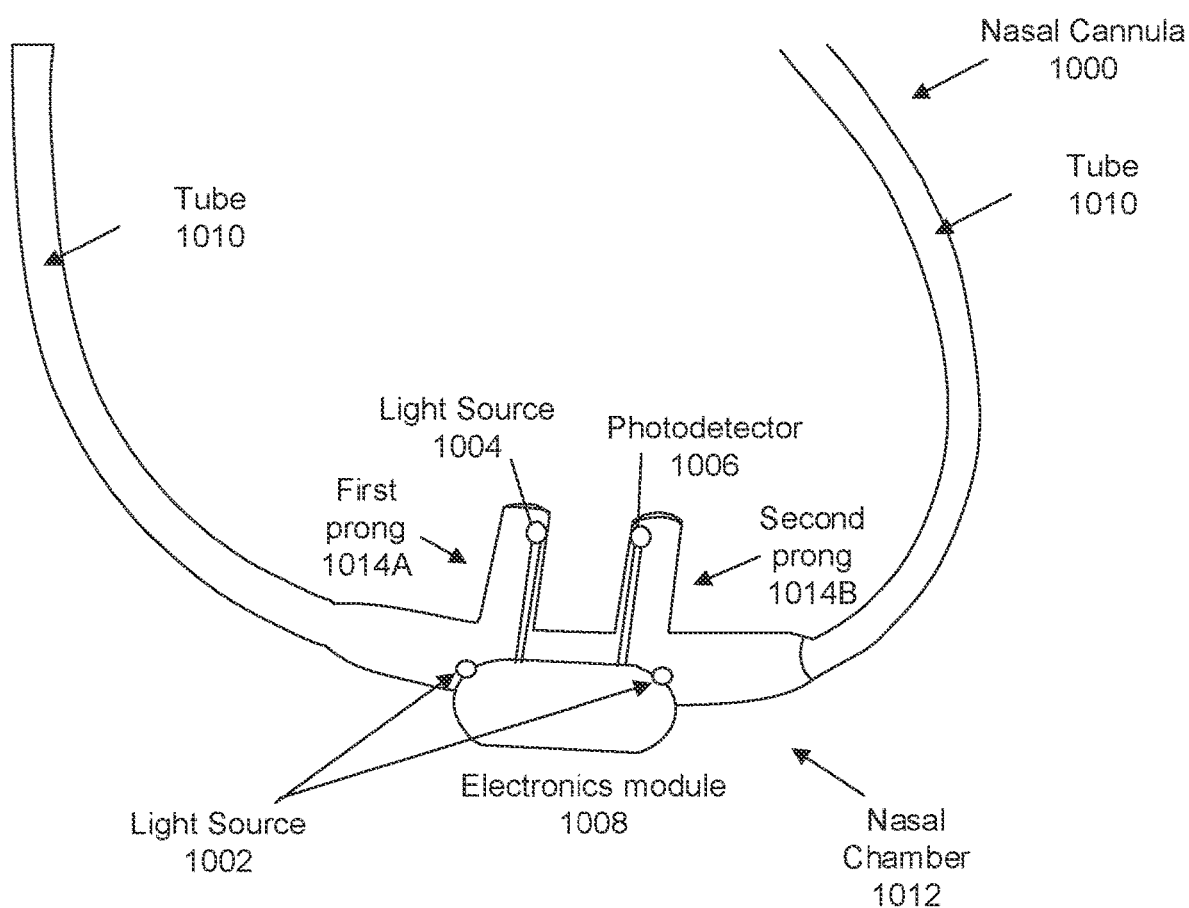
FIG. 10 illustrates another exemplary nasal cannula, according to the embodiments of the present disclosure.

Referring now to FIG. 10, another exemplary device for monitoring the respiratory status of a user, according to the embodiments of the present disclosure, is shown. The device may comprise a nasal cannula 1000 comprising a nasal chamber 1012, tube 1010, and a connector (similar to connector 408 of FIG. 4) configured to couple the nasal cannula 1000 to a remote device. In some embodiments, the remote device may comprise an oxygen concentrator. In other embodiments, the remote device may comprise a power source and/or a battery management system (BMS). As shown in FIG. 10, the nasal chamber 1012 may comprise a first prong 1014A configured to be positioned in the user's first nasal passage of the nose and a second prong 1014B configured to be positioned in the user's second nasal passage of the nose. The exemplary device of FIG. 10 may comprise surface-mount components embedded directly into each of the first prong 1014A and the second prong 1014B. For example, a light source 1004, such as a red or green LED and/or an infrared LED, may be disposed on or within the first prong 1014A, and a photodetector 1006 may be disposed on or within the second prong 1014B opposite the first prong 1014A. Accordingly, the light source 1004 may transmit light through the user's nose septum and the photodetector 1006 may receive the light passing through the user's nose septum to measure the user's respiratory parameter(s) such as oxygen saturation ($SpO_2$), heart rate, respiratory rate, and/or breathing pattern.

In some embodiments, the device of FIG. 10 may comprise an electronics module 1008 disposed on the nasal chamber 1012. The electronics module 1008 may be embedded directly on the base of the nasal chamber 1012 and may be electronically coupled to the light source 1004 and the photodetector 1006. The connection between the electronics module 1008 and the light source 1004 or photodetector 1006 may be a wired connection with one or more wires encapsulated in the first prong 1014A and the second prong 1014B and passing through the tube 1010 to a connector coupled at the other end of the tube 1010. In other embodiments, the connection between the electronics module 1008 and the light source 1004 or photodetector 1006 may be a wireless connection. The electronics module 1008 may also comprise a light source 1002, such as one or more LEDs. For example, the electronics module 1008 may comprise RGB LEDs and may be configured to transmit light via the RGB LEDs in order to provide a visual indication of the user's respiratory status. For example, the electronics module 1008 may be configured to change the color, color intensity, color pattern, or timing of the light transmitted via the light source 1002 to provide a visual indication of the user's respiratory status. When the electronics module 1008 transmits light via the RGB LEDS, the light source 1002 may be configured to illuminate at least a portion of the tube 1010 surrounding the electronics module 1008, such as the tube 1010 on either side of the electronics module 1008. The electronics module 1008 may comprise at least one processor configured to receive the light detected by the photodetector 1006 and measure one or more respiratory parameters of the user. Accordingly, because the electronics module 1008 may be configured to measure the user's respiratory parameter(s) and provide a visual indication of the user's respiratory status, via light source 1002, in real-time or near real-time, the device of FIG. 10 may not need to be connected to a processor disposed in a remote device, such as remote device 200 of FIG. 25. Instead, the device of FIG. 10 may be a standalone nasal cannula 1000 connected to a power source. The device of FIG. 10 may also be configured to wirelessly communicate with a separate oxygen concentrator and/or other remote devices.

As discussed above, the embodiments of the present disclosure may not be limited to a nasal cannula and may be a smart cannula configured to measure the user's respiratory parameter(s) when touch contact is established with one or more locations of the user's body. For example, the smart cannula may comprise a first prong configured to be disposed on a first location of a body of a user and a second prong configured to be disposed on a second location of the body of the user. By way of example, the first prong may be disposed on a first location of the user's cheek(s) and the second prong may be disposed on a second location of the user's cheek(s). Additionally, or alternatively, the first prong may be disposed on a first location of a rim and/or ridge of the user's nose and the second prong may be disposed on a second location of a rim and/or ridge of the user's nose. Additionally, or alternatively, the front prong may be disposed on a first location of a lobe and/or rim of the user's ear and the second prong may be disposed on a second location of a lobe and/or rim of the user's ear. The smart cannula may comprise a connector (such as connector 408 of FIG. 4) configured to couple the cannula to a remote device (such as remote device 200 of FIG. 2). The smart cannula may also comprise a tube (such as tube 300 of FIGS. 3 and 4) configured to couple the first prong and the second prong to the connector. The tube may define a first path between the connector and the first prong and a second path between the connector and the second prong. The smart cannula may also comprise a plurality of optical fibers (such as optical fibers 103A and 103B of FIGS. 2 and 5-8, and/or optical fibers 304 and 302 of FIG. 3) passing through at least a portion of the tube. As discussed above, the first optical fiber may be configured to transmit, via the first path, light to the first location of the body of the user, the second optical fiber may be configured to receive, via the second path, light received at the second location of the body of the user, and the third optical fiber may be configured to emit one or more visible wavelengths of light along at least a portion of a length of the tube such that the emitted light is visible from outside the tube. In other embodiments, the smart cannula may comprise an electronics module (such as electronics module 1008) coupled directly onto the tube of the smart cannula.

Figure 11:
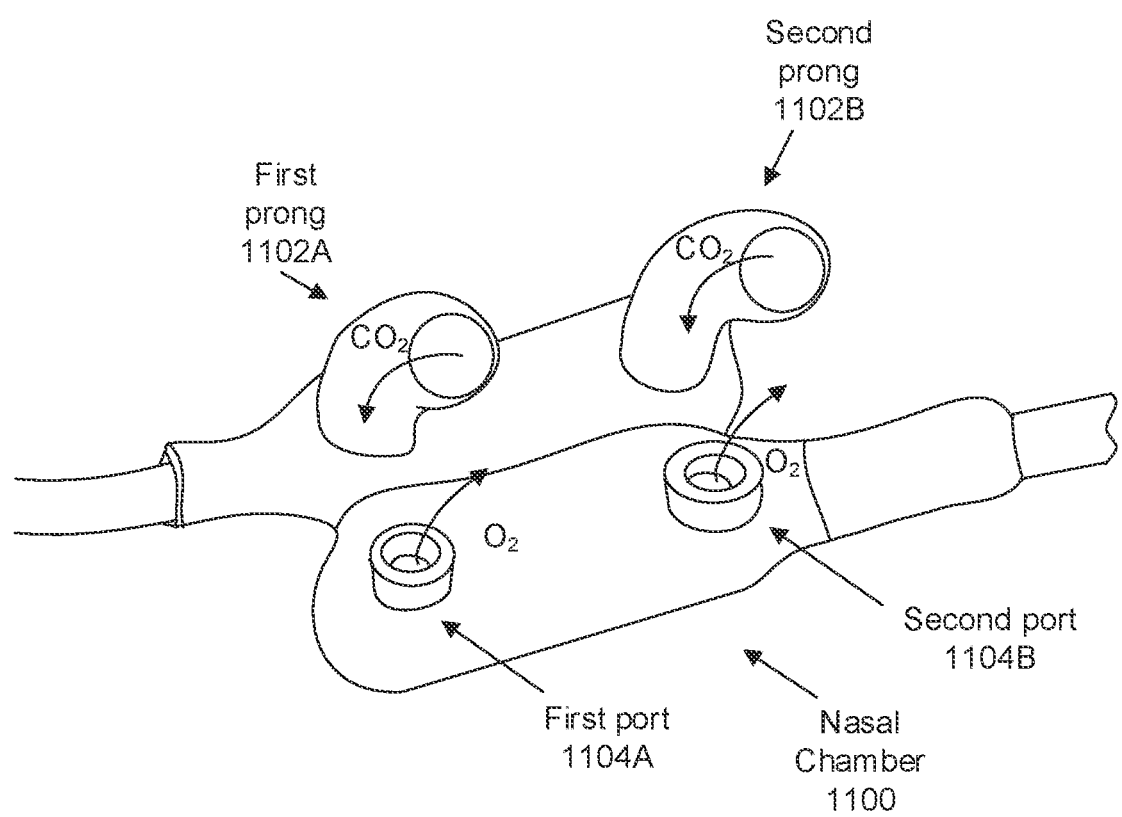
FIG. 11 illustrates another exemplary device for monitoring the respiratory status of a user, according to the embodiments of the present disclosure.

In some embodiments, the nasal cannula 202 of FIGS. 2-8 and the nasal cannula 1000 of FIG. 10 may comprise a dual-lumen cannula, as shown in FIG. 11. Accordingly, in addition to having a first prong 1102A configured to be positioned inside the user's first nasal passage and a second prong 1102B configured to be positioned inside the user's second nasal passage, the nasal cannula may comprise two additional ports (first port 1104A and second port 1104B) in the nasal chamber 1100. The first port 1104A and the second port 1104B may be configured to deliver oxygen to the user. Additionally, or alternatively, one of the first port 1104A and the second port 1104B may be configured to sense pressure inside one of the user's nostrils. Accordingly, a dual-lumen cannula, such as the one illustrated in FIG. 11, may be configured to sense, and deliver oxygen in both of the user's nostrils while minimizing risks associated with a medical condition, such as a deviated septa and occlusion, by sensing pressure at one of the two ports 1104A, 1104B and delivering oxygen to both nostrils via the first and second ports 1104A, 1104B. The signal pathways described in FIG. 8 may be similarly applied to the nasal cannula 1000 of FIG. 10.

Figure 12A:
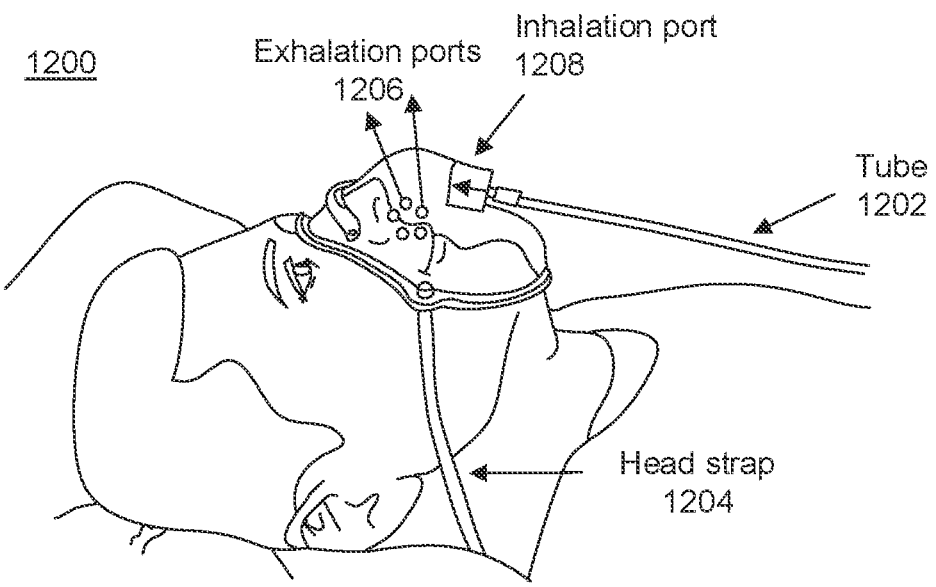
FIG. 12A illustrates another exemplary device for monitoring the respiratory status of a user, according to the embodiments of the present disclosure.
Figure 12B:
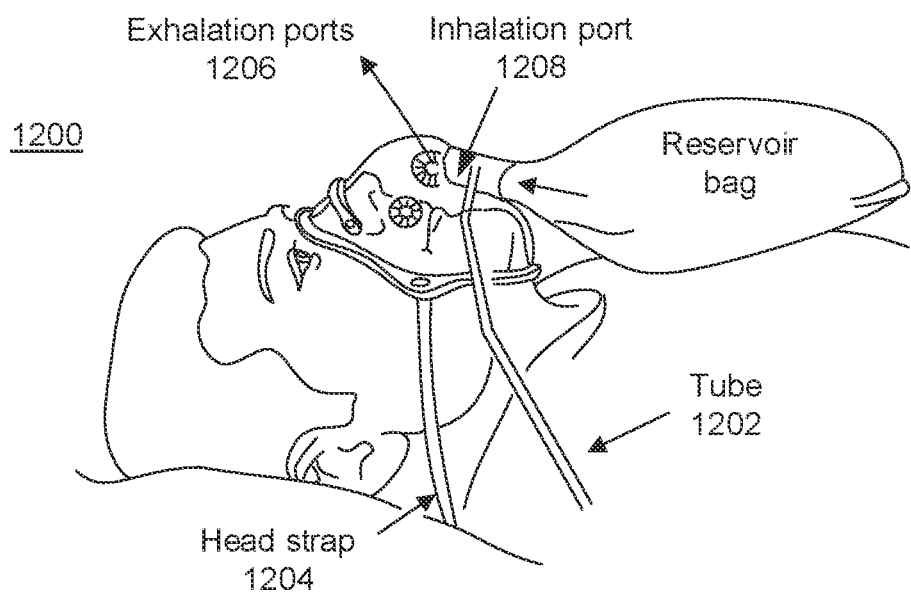
FIG. 12B illustrates another exemplary device for monitoring the respiratory status of a user, according to the embodiments of the present disclosure.

In other embodiments, the system for monitoring the user's respiratory status and delivering oxygen to the user may comprise a face/venturi mask in conjunction with the nasal cannula methods outlined above. By way of example, as shown in FIGS. 12A and 12B, a face and venturi mask may comprise an inhalation port 1208, one or more exhalation ports 1206, and an elastic head strap 1204 configured to secure the mask on the user's head. As shown in FIGS. 12A and 12B, the mask may comprise a tube 1202 connected to the inhalation port 1208 and configured to couple the mask to a remote device, such as an oxygen source, to deliver oxygen to the user. In some embodiments, as shown in FIG. 12B, the mask may be coupled to a reservoir bag. The reservoir bag may be configured to increase the inhaled oxygen concentration by preventing oxygen loss during inhalation.

In some embodiments, one or more optical fibers may be attached to the tube 1202. One or more optical fibers may comprise a side-emitting optical fiber, such as the side-emitting optical fiber 302 of FIG. 3. Like the side-emitting optical fiber 302, one or more optical fibers attached to the tube 1202 may provide a visual indication of the user's respiratory status. For example, the tube 1202 may be connected to a remote device, such as remote device 200 of FIG. 2, comprising a light source (e.g., one or more RGB LEDs). A processor in the remote device may measure the user's respiratory parameter(s) and simultaneously provide a visual indication of the user's respiratory status by transmitting light via one or more RGB LEDs through the one or more optical fibers attached to the tube 1202. The light may be transmitted along the length of the tube 1202 such that the light is visible from outside of the tube 1202. The color, color intensity, pattern, and/or timing of the light transmitted along the tube 1202 may vary based on the user's respiratory status.

Figure 13:
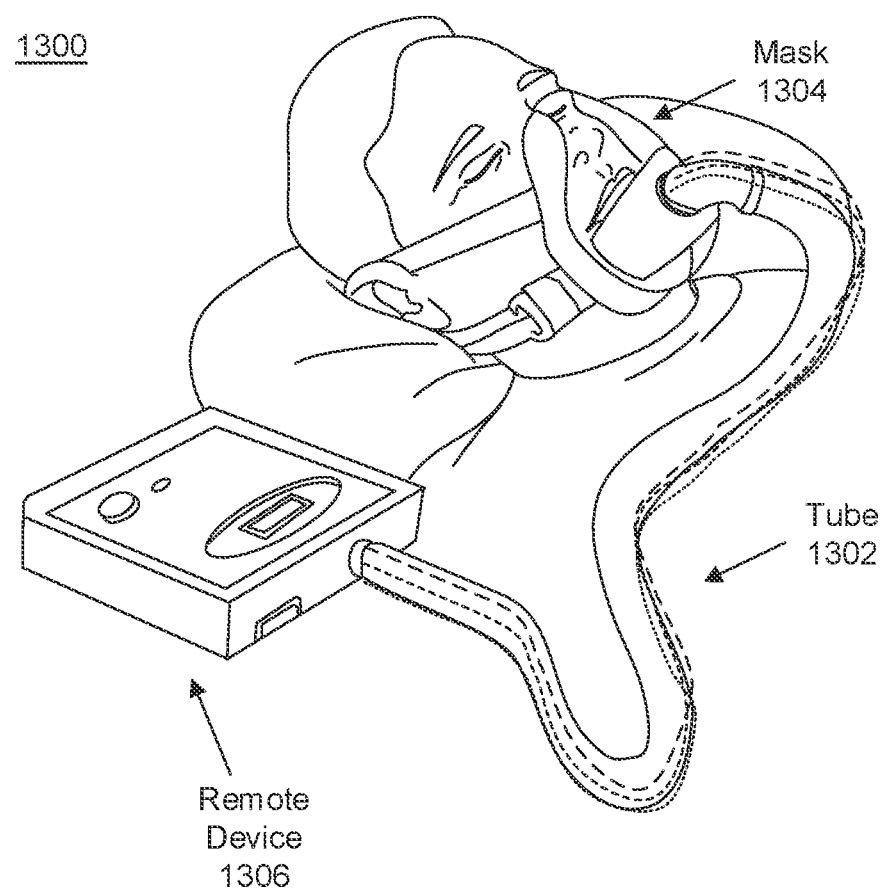
FIG. 13 illustrates another exemplary device for monitoring the respiratory status of a user, according to the embodiments of the present disclosure.

In yet another embodiment, the system for monitoring the user's respiratory status and delivering oxygen to the user may comprise a continuous positive airway pressure (CPAP) or non-invasive ventilation (NIV) mask in conjunction with the measurement or titration system. For example, as shown in FIG. 13, a CPAP mask 1304 may be coupled to a remote device 1306 via tube 1302. The remote device 1306 may be similar to the remote device 200 of FIG. 2 and may comprise a light source (e.g., RGB LED(s)), a processor, a sensor module, or the like. The remote device 1306 may comprise a processor configured to measure one or more respiratory parameters of the user based on the user's breath received by the mask 1304. In addition, a sensor module (similar to the sensor module 210 of FIG. 2) in the remote device 1306 may be configured to monitor the user's respiratory status. For example, the sensor module may comprise photoplethysmography sensor (PPG), electroencephalogram (EEG) sensors, electromyography (EMG) sensors, electrocardiogram (ECG) sensors, pulse transit time (PTT) sensors, gas flow sensors, temperature sensors, microphones, blood oxygen meters, blood pressure sensors, pulse sensors, patient movement sensor, position sensor, light sensor such as a photodetector, activity sensors, mask leakage sensor, pressure sensor, piezo sensors, or the like. The sensor module may be configured to also measure respiratory rate, eye movement, respiratory rate, sound (e.g., to diagnose the decibels (dB) of cough), or the like.

As discussed with respect to FIGS. 12A and 12B, the CPAP or NIV mask 1304 may also comprise one or more optical fibers attached to the tube 1302. One or more optical fibers may comprise a side-emitting optical fiber, such as the side-emitting optical fiber 302 of FIG. 3. Like the side-emitting optical fiber 302, one or more optical fibers attached to the tube 1302 may provide a visual indication of the user's respiratory status. For example, the remote device 1306 may comprise a light source, such as one or more RGB LEDs. A processor in the remote device 1306 may measure the user's respiratory parameter(s) and simultaneously provide a visual indication of the user's respiratory status by transmitting light via one or more RGB LEDs through the one or more optical fibers attached to the tube 1302. The light may be transmitted along the length of the tube 1302 such that the light is visible from outside of the tube 1302. The color, color intensity, pattern, and/or timing of the light transmitted through the tube 1302 may vary based on the user's respiratory status.

While the present disclosure is described herein with reference to illustrative embodiments of a smart nasal cannula used for particular applications, such as for monitoring the user's respiratory status and providing concentrated oxygen to the user, it should be understood that the embodiments described herein are not limited thereto. Those having ordinary skill in the art and access to the teachings provided herein will recognize additional modifications, applications, embodiments, and substitution of equivalents that all fall within the scope of the disclosed embodiments. Accordingly, the disclosed embodiments are not to be considered as limited by the foregoing or following descriptions.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A system for monitoring respiratory status of a user, comprising:
    a nasal cannula including a first prong configured to be inserted into a first nasal passage of the user and a second prong configured to be inserted into a second nasal passage of the user;
    a light transmitter coupled to a first optical fiber, wherein the light transmitter is configured to transmit, via the first optical fiber and the first prong, a first light to the first nasal passage of the user;
    a photodetector coupled to a second optical fiber, wherein the photodetector is configured to receive, via the second prong and the second optical fiber, a second light from the second nasal passage of the user, the second light being at least a portion the first light that passes into the second nasal passage from the first nasal passage;
    at least one processor configured to detect a difference in a characteristic between the first light and the second light and determine one or more respiratory parameters associated with the respiratory status based at least partly on the detected difference; and
    a third optical fiber configured to provide a visual indication of the determined results for one or more respiratory parameters;
    wherein the first optical fiber, the second optical fiber, and the third optical fiber extend at least part way through a tube connected to the nasal cannula, and wherein the third optical fiber is configured to (a) display light of a first color if at least one of the determined one or more respiratory parameters is above a target range, (b) display light of a second color if the at least one of the determined one or more respiratory parameters is below the target range, and (c) display light of a third color if the at least one of the determined one or more respiratory parameters is within the target range.

2. The system of claim 1, wherein the characteristic includes at least one of intensity, wavelength, frequency, color, polarization, phase, direction, speed, polarization state, or dispersion.

3. The system of claim 1, wherein the first light includes a plurality of wavelengths, and the at least one processor is configured to detect the difference in absorbance at each of the plurality of wavelengths between the first light and the second light.

4. The system of claim 1, wherein the one or more respiratory parameters include at least one of an oxygen saturation (SpO2) level, a heart rate, a respiratory rate, a perfusion index, or a breathing pattern.

5. The system of claim 1, further including an oxygen concentrator configured to direct oxygen to the user via the nasal cannula, wherein the at least one processor is configured to adjust one or more of a concentration or a flow rate of the oxygen directed to the user based on the determined one or more respiratory parameters.

6. The system of claim 5, wherein the oxygen concentrator is a portable oxygen concentrator.

7. The system of claim 1, wherein the visual indication includes displaying light of a first color if at least one of the determined one or more respiratory parameters is above a threshold value and displaying light of a second color if at least one of the determined one or more respiratory parameters is below a threshold value.

8. The system of claim 1, further including an indicator configured to provide a visual indication of an incorrect positioning of the first and second prongs of the nasal cannula on the user.

9. A method of monitoring respiratory status of a user, comprising:
discharging, from a light transmitter, first light into a first nasal passage of the user via a first prong of a nasal cannula inserted into the first nasal passage;
receiving, at a photodetector, second light from a second nasal passage of the user via a second prong of the nasal cannula inserted into the second nasal passage, wherein the second light includes at least a portion of the first light that passes into the second nasal passage from the first nasal passage;
using at least one processor to (i) detect a difference in a characteristic between the first light and the second light, and (ii) determine one or more respiratory parameters associated with the respiratory status based at least partly on the detected difference; and
providing a visual indication of the determined results for one or more respiratory parameters via a third optical fiber;
wherein the first optical fiber, the second optical fiber, and the third optical fiber extend at least part way through a tube connected to the nasal cannula, and wherein the third optical fiber is configured to (a) display light of a first color if at least one of the determined one or more respiratory parameters is above a target range, (b) display light of a second color if the least one of the determined one or more respiratory parameters is below the target range, and (c) display light of a third color if the at least one of the determined one or more respiratory parameters is within the target range.

10. The method of claim 9, wherein the characteristic includes at least one of intensity, wavelength, frequency, color, polarization, phase, direction, speed, polarization state, or dispersion, and wherein the one or more respiratory parameters include at least one of an oxygen saturation (SpO2) level, a heart rate, a respiratory rate, a perfusion index, or a breathing pattern.

11. The method of claim 9, further including directing oxygen to the user via the nasal cannula and adjusting one or more of a concentration or a flow rate of the oxygen directed to the user based on the determined one or more respiratory parameters.

12. The method of claim 9, further including providing a visual indication of the determined one or more respiratory parameters via an optical fiber connected to the nasal cannula.

13. The method of claim 12, wherein the visual indication includes (a) displaying light of a first color if at least one of the determined one or more respiratory parameters is above a target range, (b) displaying light of a second color if the least one of the determined one or more respiratory parameters is below the target range, and (c) displaying light of a third color if the at least one of the determined one or more respiratory parameters is within the target range.

14. A device for monitoring respiratory status of a user, comprising:
a nasal cannula including a first prong configured to be inserted into a first nasal passage of a user and a second prong configured to be inserted into a second nasal passage of a user;
a connector configured to couple the nasal cannula to a remote device; and
a tube configured to couple a nasal chamber to the connector; and
a plurality of optical fibers passing through at least a portion of the tube, wherein (a) a first optical fiber of the plurality of optical fibers is configured to transmit light to the first nasal passage of the user, (b) a second optical fiber of the plurality of optical fibers is configured to receive light passing through a nose septum and into the second nasal passage of the user, and (c) a third optical fiber attached to the tube and configured to emit one or more visible wavelengths of light such that the emitted light is visible from outside the tube;
wherein the third optical fiber is a side-emitting optical fiber configured to emit different visible wavelengths of light, wherein a color of the light emitted via the third optical fiber is indicative of the respiratory status of the user.

15. The device of claim 14, wherein the third optical fiber is configured to emit a first visible wavelength of light when a measured respiratory parameter of the user is within a first range and a second visible wavelength of light when the measured respiratory parameter of the user is within a second range.

16. The device of claim 14, wherein a color intensity, a color pattern, or a timing of the light emitted via the third optical fiber is configured to change based on the respiratory status of the user.

17. A system for monitoring respiratory status of a user, comprising:
a nasal cannula including a first prong configured to be inserted into a first nasal passage of the user and a second prong configured to be inserted into a second nasal passage of the user;
a light transmitter coupled to a first optical fiber, wherein the light transmitter is configured to transmit, via the first optical fiber and the first prong, a first light to the first nasal passage of the user;
a photodetector coupled to a second optical fiber, wherein the photodetector is configured to receive, via the second prong and the second optical fiber, a second light from the second nasal passage of the user, the second light being at least a portion the first light that passes into the second nasal passage from the first nasal passage; and
at least one processor configured to detect a difference in a characteristic between the first light and the second light and determine one or more respiratory parameters associated with the respiratory status based at least partly on the detected difference,
wherein the nasal cannula further includes a third optical fiber, the third optical fiber being configured to provide both (a) a visual indication of an incorrect positioning of the nasal cannula on the user, and (b) a visual indication of the respiratory status of the user in real-time.

18. The system of claim 17, wherein the characteristic includes at least one of intensity, wavelength, frequency, color, polarization, phase, direction, speed, polarization state, or dispersion.

19. The system of claim 17, wherein the one or more respiratory parameters include at least one of an oxygen saturation (SpO2) level, a heart rate, a respiratory rate, a perfusion index, or a breathing pattern.

20. The system of claim 17, further including an oxygen concentrator configured to direct oxygen to the user via the nasal cannula, wherein the at least one processor is configured to adjust one or more of a concentration or a flow rate of the oxygen directed to the user based on the determined one or more respiratory parameters.

* * * * *

UNITED STATES PATENT AND TRADEMARK OFFICE
CERTIFICATE OF CORRECTION

PATENT NO. : 12,121,662 B2
APPLICATION NO. : 18/385990
DATED : October 22, 2024
INVENTOR(S) : Shan-Shan Wang et al.

Page 1 of 1

It is certified that error appears in the above-identified patent and that said Letters Patent is hereby corrected as shown below:

In the Claims

Claim 1, Column 16, Line 37, "at least a portion the" should read --at least a portion of the--.

Claim 17, Column 18, Line 62, "at least a portion the" should read --at least a portion of the--.

Signed and Sealed this
Eighteenth Day of February, 2025

Coke Morgan Stewart
*Acting Director of the United States Patent and Trademark Office*